United States Patent
Corso

Patent Number: 5,876,346
Date of Patent: Mar. 2, 1999

[54] ARTERY LOCATING DEVICE

[76] Inventor: Albert Mario Corso, 175 Randall Rd., Shoreham, N.Y. 11786

[21] Appl. No.: 726,045

[22] Filed: Oct. 7, 1996

[51] Int. Cl.$^6$ .......................................................... A61B 5/00
[52] U.S. Cl. ............................ 600/485; 600/500; 600/503
[58] Field of Search .................................. 600/500–503, 600/485

[56] References Cited

U.S. PATENT DOCUMENTS

| | | | |
|---|---|---|---|
| 5,195,522 | 3/1993 | Pytel et al. | 600/503 |
| 5,271,405 | 12/1993 | Boyer et al. | 600/503 |
| 5,467,771 | 11/1995 | Narimatsu | 600/500 |
| 5,485,848 | 1/1996 | Jackson et al. | 600/500 |
| 5,494,043 | 2/1996 | O'Sullven et al. | 600/500 |
| 5,497,779 | 3/1996 | Takaya et al. | 500/503 |
| 5,579,777 | 12/1996 | Suga | 600/503 |
| 5,617,867 | 4/1997 | Butterfield et al. | 600/503 |

*Primary Examiner*—Robert L. Nasser
*Attorney, Agent, or Firm*—Michael I. Kroll

[57] ABSTRACT

The present invention relates to an artery locating device (10) which comprises a housing (18) comprising a housing power means access (18A), a housing bottom (18B), a housing front (18F), and a housing rear (18R). The artery locating device (10) further comprises a microchip (22) contained within the housing (18). The artery locating device (10) further comprises a power means (24) electronically connected to the microchip (22). The artery locating device (10) further comprises a heart rate monitor (12) is contained within the housing (18). The heart rate monitor (12) comprises a heart rate monitor LCD display (12B) which is electronically connected to the microchip (22). The heart rate monitor (12) further comprises a heart rate monitor visual display (12C) having a heart rate monitor visual display indicator light (12CA) which is electronically connected to the microchip (22). The artery locating device (10) further comprises a pulse intensity monitor (14) contained within the housing (18). The pulse intensity monitor (14) comprises a pulse intensity monitor LCD display (14B) which is electronically connected to the microchip (22). The pulse intensity monitor (14) further comprises a pulse intensity monitor visual display (14C) having a pulse intensity monitor visual display indicator light (14CA) which is electronically connected to the microchip (22). The artery locating device (10) further comprises an artery monitor (16) contained within the housing (18). The artery monitor (16) comprises an artery monitor visual display (16A) which is electronically connected to the microchip (22). The artery monitor (16) further comprises an artery monitor visual display indicator light (16AA) which is electronically connected to the microchip (22). The artery locating device (10) further comprises an artery sensor (20) contained within the housing (18) positioned at the housing bottom (18B). The artery sensor (20) is electronically connected to the microchip (22).

10 Claims, 5 Drawing Sheets

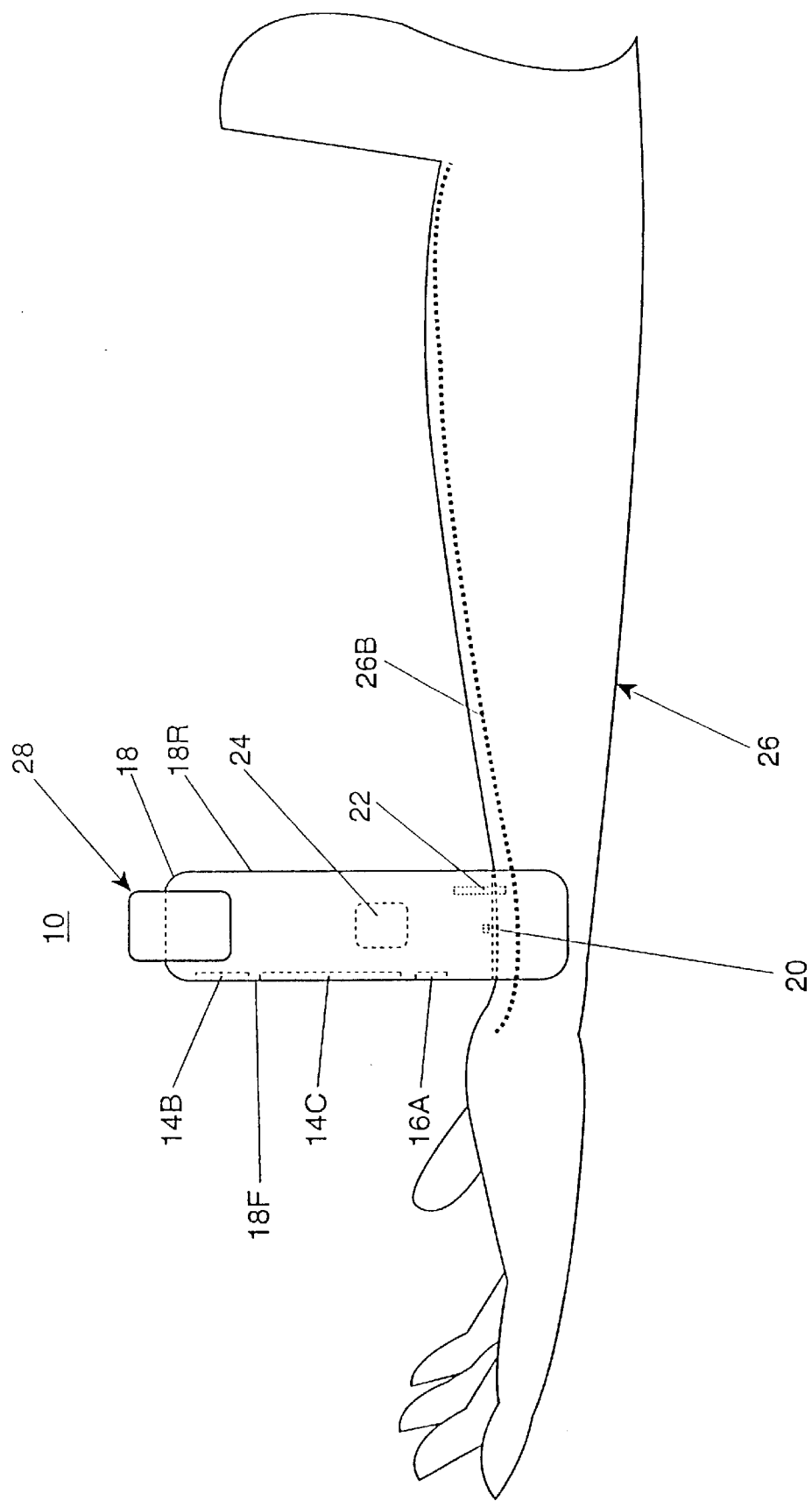

110

| 112 | placing (112) a housing bottom (18B) of an artery locating device (10) on a patient's arm epidermis (26A) |

| 114 | first moving (114) the artery locating device (10) laterally until a patient's arm artery (26B) is detected by an artery sensor (20) activating an artery monitor (16) |

| 116 | second moving (116) the artery locating device (10) laterally until a patient's arm artery (26B) is centered by indication of an artery monitor visual display indicator light (16AA) of an artery monitor visual display (16A) |

FIG 3

ARTERY LOCATING DEVICE

BACKGROUND OF THE INVENTION

1. Field of the Invention

The present invention relates to an artery locating device. More particularly, the present invention relates to an artery locating device which is portable and comprises a heart rate monitor, a pulse intensity monitor and a artery monitor contained in one housing.

2. Description of the Prior Art

Certain medical procedures require venipuncture and therefore exact location of veins and arteries beneath the skin of a living body. The current most frequently utilized technology utilizes a visual scan of a medical person to locate and puncture the vein or artery. However, this technique is extremely inaccurate when the veins or arteries are deep underneath the skin making visualization impossible. Missing the vein or artery when inserting a needle causes sub-cutaneous hemorrhaging having disastrous or fatal medical effects.

Numerous innovations for artery locating device have been provided in the prior art that are described as follows. Even though these innovations may be suitable for the specific individual purposes to which they address, they differ from the present invention as hereinafter contrasted.

In Patent number, titled Time Calculating Device, invented by Fusao Suga, a time calculating device calculates a time which a user of the device requires to run a distance such as a whole distance of a marathon race. The time calculating device is provided with a pulse frequency memory which measures pulse frequencies of the user when the user runs a given distance at least twice at predetermined different paces, and which stores the measured pulse frequencies. The time calculating device is further provided with an age input key for inputting age data of the user, and a distance input key for inputting a distance. A running speed at which the user of an age can keep running continuously is calculated from the pulse frequencies stored in the pulse frequency memory and age data input by the age input key. Further, a time is calculated which the user requires to run the distance inputted by the distance input key at the calculated running speed. The calculated time is displayed on a display unit of the time calculating device.

In U.S. Pat. No. 5,273,046, titled Method of Determining Optimum Artery Applanation, invented by Robert D. Butterfield and Stephen A. Martin, a method, for use in a non-invasive blood pressure monitoring system, of determining optimum artery applanation. The system uses a stress sensor including a stress sensitive element for detecting stress of tissue overlying an artery of interest. The tissue stress sensor is placed in communication with tissue overlying the artery of interest and at least one electrical signal is obtained therefrom representing stress data across the length of the stress sensitive element. The data represents stress datum communicated to a preselected portion of the stress sensitive element. From the stress datum, various algorithms are used, singly or in combination, to provide the best measure of optimum applanation state. Intra-arterial blood pressure is then calculated using datum collected at the optimum applanation state. In addition, to the optimum applanation methods, a method is disclosed for determining which portion of the stress sensitive element is best suited for estimating intra-arterial blood pressure.

In U.S. Pat. No. 4,867,170, Titled Measuring Apparatus for Blood Pressure, invented by Masakatsu Takahashi, a measuring apparatus for blood pressure comprises a blood pressure measuring portion and a holder pipe. The blood pressure measuring portion comprises a device for searching a location of an artery appropriate for blood pressure measurement and for detecting a pulse by being pressed on a skin surface above or near the artery. A device is provided for detecting blood pressure, a device for block blood stream, a portion for indicating a measured value of blood pressure and a portion for indicating a detected pulse of the artery appropriate for measurement are also provided. The blood pressure measuring portion is inserted slidably in the holder pipe. The holder pipe is equipped removably with a strap for fixing the holder pipe.

In U.S. Pat. No. 4,425,921, titled Apparatus for Checking Pulse and Heart Rates, invented by Iwao Fujisaki, Shuichi Kosuge, Syuu Ogawa, Kimihiko Sato and Toshini Soeda, a small portable-type apparatus for checking pulse or heart rate of a person engaged in exercise. Therefore, the apparatus according to the present invention can be used as a pulsimeter or a cardiometer according to the state of a person in motion. The apparatus is provided with a heart sensor having a plurality of cone-shaped conductive rubber electrodes to differentially detect an electrocardiowave voltage signal generated from three different places near the heart and a pulse sensor having a matching infrared-ray emitting diode and infrared-ray receiving photo transistor to detect the light reflected from the blood flowing through capillary vessels under the finger pad. The apparatus additionally functions as a stopwatch or a timer as selected by a mode-selector switch.

In U.S. Pat. No. 4,163,447, Titled Heartbeat Rate Monitor, invented by Thomas Orr, a heartbeat rate monitor has a light source, powered by a rechargeable battery, for transilluminating skin tissue. A semiconductor which produces an output signal in dependence on light originating from the light source and reflected from the skin tissue, and hence on changes in arterial blood flow, is additionally used, on exposure to ambient light, to produce a current for recharging the battery.

In U.S. Pat. No. 3,745,989, titled Device for Locating Veins in Living Bodies, invented by Sanford Pinna, a casing is provided with an elongated sensor rod and a marking rod mounted for axial reciprocation by a motor driven cam through compression springs so that the sensor is moved outwardly of the casing by a constant force with the end of the sensor engaging a living body so that the distance of outward movement depends on the resistance of the body, a latch release lug extends on the resistance of the body, a latch release lug extends from the sensor to release a spring urged marking rod for outward movement to mark the surface of the body in response to movement of the sensor rod beyond a given position in response to lessened resistance to outward movement of the sensor occasioned by a vein positioned beneath the sensor.

The present invention differs from the above described patented inventions because they lack one or more of the following features: a heart rate monitor, a pulse intensity monitor, an artery monitor, an artery sensor, and a digital finger clip.

Numerous innovations for artery locating device have been provided in the prior art that are adapted to be used. Even though these innovations may be suitable for the specific individual purposes to which they address, they would not be suitable for the purposes of the present invention as heretofore described.

SUMMARY OF THE INVENTION

The present invention relates to an artery locating device. More particularly, the present invention relates to an artery locating device which is portable and comprises a heart rate monitor, a pulse intensity monitor and a artery monitor contained in one housing.

The types of problems encountered in the prior art are visualization of veins or arteries is imprecise and dangerous.

In the prior art, unsuccessful attempts to solve this problem were attempted namely: probing type vein or artery locators. However, the problem was solved by the present invention because the location of the vein or artery is accomplished by a artery sensor in conjunction with a microchip.

Innovations within the prior art are rapidly being exploited in the field of medical research and medical equipment.

The present invention went contrary to the teaching of the art which describes and claims probing type artery sensing devices as well as pulse and heart rate detecting devices.

The present invention solved a long felt need for a single compact device to perform all required medical procedures such as heart rate, pulse intensity and artery location in one piece of equipment.

Accordingly, it is an object of the present invention to provide an artery locating device which comprises a heart rate monitor, a pulse intensity monitor, an artery monitor, an artery sensor, a microchip, a power means, and a digital finger clip all enclosed within a single housing.

More particularly, it is an object of the present invention to provide the heart rate monitor which comprises heart rate monitor indicia, heart rate monitor LCD display, heart rate monitor visual display, and heart rate monitor visual display indicator light.

In keeping with these objects, and with others which will become apparent hereinafter, one feature of the present invention resides, briefly stated, in the pulse intensity monitor comprising pulse intensity monitor indicia, a pulse intensity monitor LCD display, a pulse intensity monitor visual display, and a pulse intensity monitor visual display indicator light.

When the artery monitor is designed in accordance with the present invention, it comprises an artery monitor visual display and an artery monitor visual display indicator light.

In accordance with another feature of the present invention, the digital finger clip comprises a digital finger clip cylinder, a digital finger clip connector, and a digital finger clip pivot pin.

Another feature of the present invention is that the housing comprises a housing power means access, a housing bottom, a housing front, and a housing rear.

The novel features which are considered characteristic for the invention are set forth in the appended claims. The invention itself however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

10—artery locating device (10)
12—heart rate monitor (12)
12A—heart rate monitor indicia (12A)
12B—heart rate monitor LCD display (12B)
12C—heart rate monitor visual display (12C)
12CA—heart rate monitor visual display indicator light (12CA)
14—pulse intensity monitor (14)
14A—pulse intensity monitor indicia (14A)
14B—pulse intensity monitor LCD display (14B)
14C—pulse intensity monitor visual display (14C)
14CA—pulse intensity monitor visual display indicator light (14CA)
16—artery monitor (16)
16A—artery monitor visual display (16A)
16AA—artery monitor visual display indicator light (16AA)
18—housing (18)
18A—housing power means access (18A)
18B—housing bottom (18B)
18F—housing front (18F)
18R—housing rear (18R)
20—artery sensor (20)
22—microchip (22)
24—power means (24)
26—patient's arm (26)
26A—patient's arm epidermis (26A)
26B—patient's arm radial artery (26B)
26C—patient's arm muscle (26C)
26D—patient's arm bone (26D)
28—digital finger clip (28)
28A—digital finger clip cylinder (28A)
28B—digital finger clip connector (28B)
28C—digital finger clip pivot pin (28C)

METHOD (110) OF UTILIZING AN ARTERY LOCATING DEVICE (10)

112—placing (112) a housing bottom (18B) of an artery locating device (10) on a patient's arm epidermis (26A)
114—first moving (114) the artery locating device (10) laterally until a patient's arm radial artery (26B) is detected by an artery sensor (20) activating an artery monitor (16)
116—second moving (116) the artery locating device (10) laterally until a patient's arm radial artery (26B) is centered by indication of an artery monitor visual display indicator light (16AA) of an artery monitor visual display (16A)

BRIEF DESCRIPTION OF THE DRAWING

FIG. 2 is a side view of an artery locating device positioned on a patient's arm epidermis on top of a patient's arm radial artery.

FIG. 3 is a diagrammatic representation of a method of utilizing an artery locating device.

DESCRIPTION OF THE PREFERRED EMBODIMENT

Figure 1:
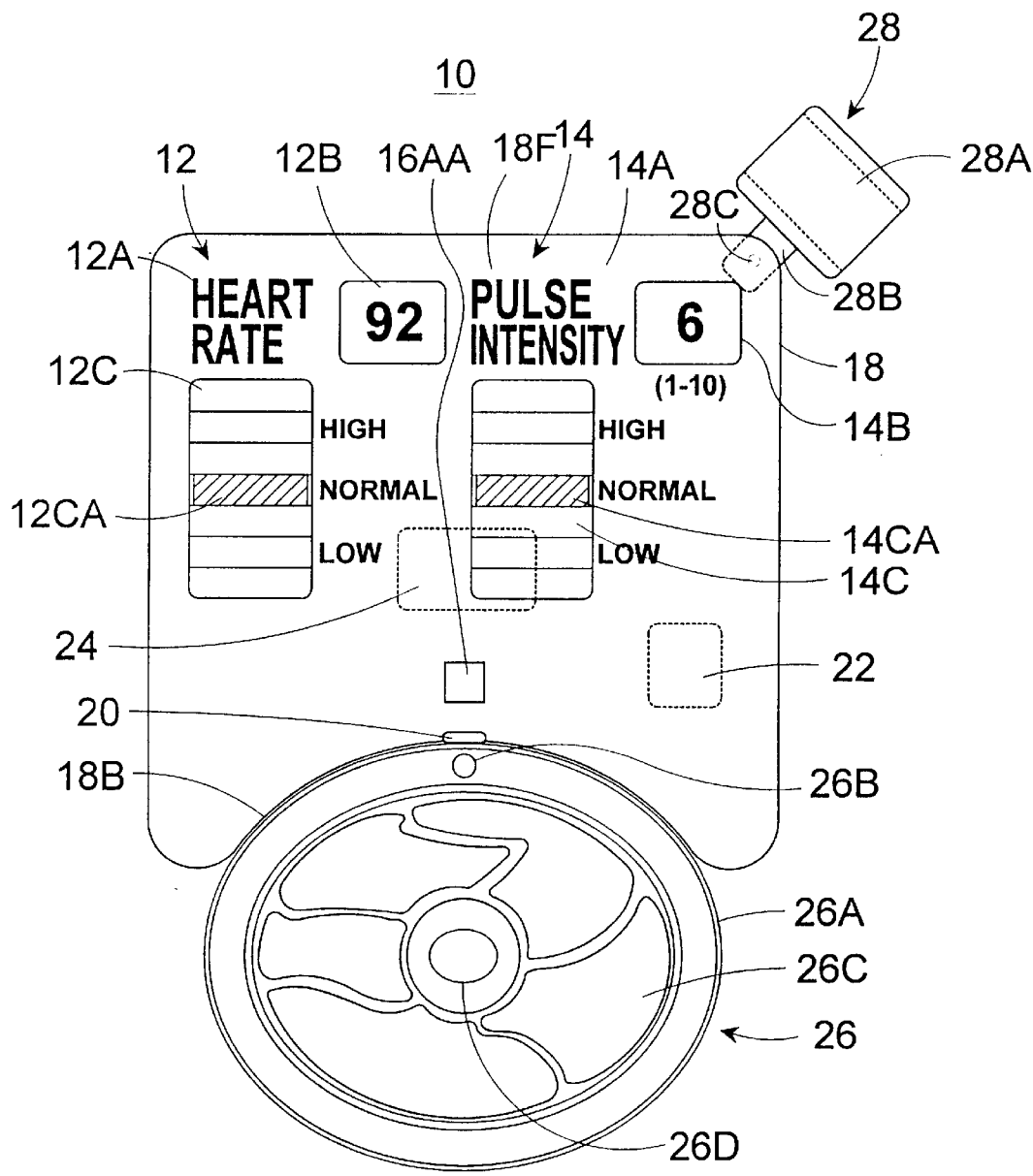
FIG. 1 is a front view of an artery locating device.

Firstly, referring to FIG. 1 which is a front view of an artery locating device (10) which comprises a housing (18) comprising a housing power means access (18A), a housing bottom (18B), a housing front (18F), and a housing rear (18R). The artery locating device (10) further comprises a microchip (22) contained within the housing (18). The housing (18) is constructed from a material selected from a group consisting of metal. Metal alloy, plastic, plastic composite, rubber, rubber composite, fiberglass, epoxy, and carbon-graphite.

The artery locating device (10) further comprises a power means (24) electronically connected to the microchip (22). The power means (24) is contained within the housing (18) having the housing power means access (18A) removably positioned there over.

The artery locating device (10) further comprises a heart rate monitor (12) is contained within the housing (18). The heart rate monitor (12) comprises a heart rate monitor LCD display (12B) which is electronically connected to the microchip (22). The heart rate monitor (12) further comprises a heart rate monitor visual display (12C) having a heart rate monitor visual display indicator light (12CA) which is electronically connected to the microchip (22). The heart rate monitor (12) further comprises heart rate monitor indicia (12A) printed thereon. The heart rate monitor (12) is preferably positioned on the housing front (18F).

The artery locating device (10) further comprises a pulse intensity monitor (14) contained within the housing (18). The pulse intensity monitor (14) comprises a pulse intensity monitor LCD display (14B) which is electronically connected to the microchip (22). The pulse intensity monitor (14) further comprises a pulse intensity monitor visual display (14C) having a pulse intensity monitor visual display indicator light (14CA) which is electronically connected to the microchip (22). The pulse intensity monitor (14) further comprises pulse intensity monitor indicia (14A) printed thereon. The pulse intensity monitor (14) is preferably positioned on the housing front (18F).

The artery locating device (10) further comprises an artery monitor (16) contained within the housing (18). The artery monitor (16) comprises an artery monitor visual display (16A) which is electronically connected to the microchip (22). The artery monitor (16) further comprises an artery monitor visual display indicator light (16AA) which is electronically connected to the microchip (22). The artery monitor (16) is preferably positioned on the housing front (18F).

The artery locating device (10) further comprises an artery sensor (20) contained within the housing (18) positioned at the housing bottom (18B). The artery sensor (20) is electronically connected to the microchip (22).

Figure 1A:
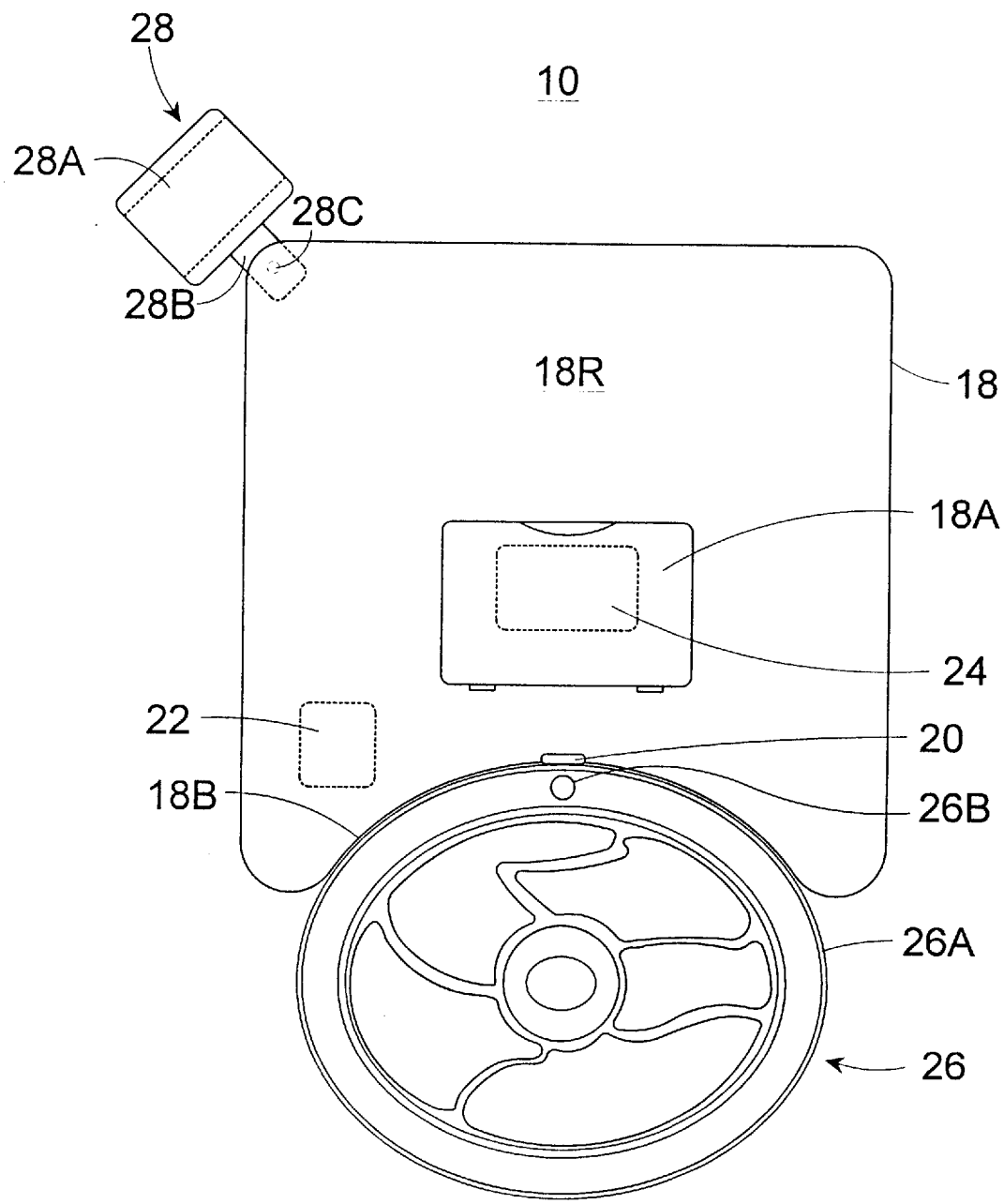
FIG. 1A is a rear view of an artery locating device.

Referring to FIG. 1A which is a rear view of an artery locating device (10). The power means (24) is preferably positioned on within the housing rear (18R) having the housing power means access (18A) positioned there over. The artery locating device (10) as described in claim 1 further comprises a digital finger clip (28) which is attached to the housing (18), the digital finger clip (28) is electrically connected to the microchip (22), when the patient inserts a finger into the digital finger clip (28) an electronic signal is sent to the microchip (22) which in turn sends an electronic signal to the artery monitor visual display indicator light (16AA) of the artery monitor visual display (16A) which functions to illuminate the artery monitor visual display indicator light (16AA), simultaneously, the microchip (22) sends an electronic signal to heart rate monitor visual display indicator light (12CA) which functions to illuminate the heart rate monitor visual display indicator light (12CA), simultaneously, the microchip (22) sends an electronic signal to the heart rate monitor LCD display (12B) which displays a patient's heart rate, simultaneously, the microchip (22) sends an electronic signal to the pulse intensity monitor visual display indicator light (14CA) which functions to illuminate the pulse intensity monitor visual display indicator light (14CA). Simultaneously, the microchip (22) sends an electronic signal to the pulse intensity monitor LCD display (14B) which displays the patient's pulse intensity. The digital finger clip (28) comprises a digital finger clip cylinder (28A) securely connected to an upper distal end of a digital finger clip connector (28B). A lower distal end of the digital finger clip connector (28B) is movably connected to the housing (18) by a digital finger clip pivot pin (28C).

Figure 2A:
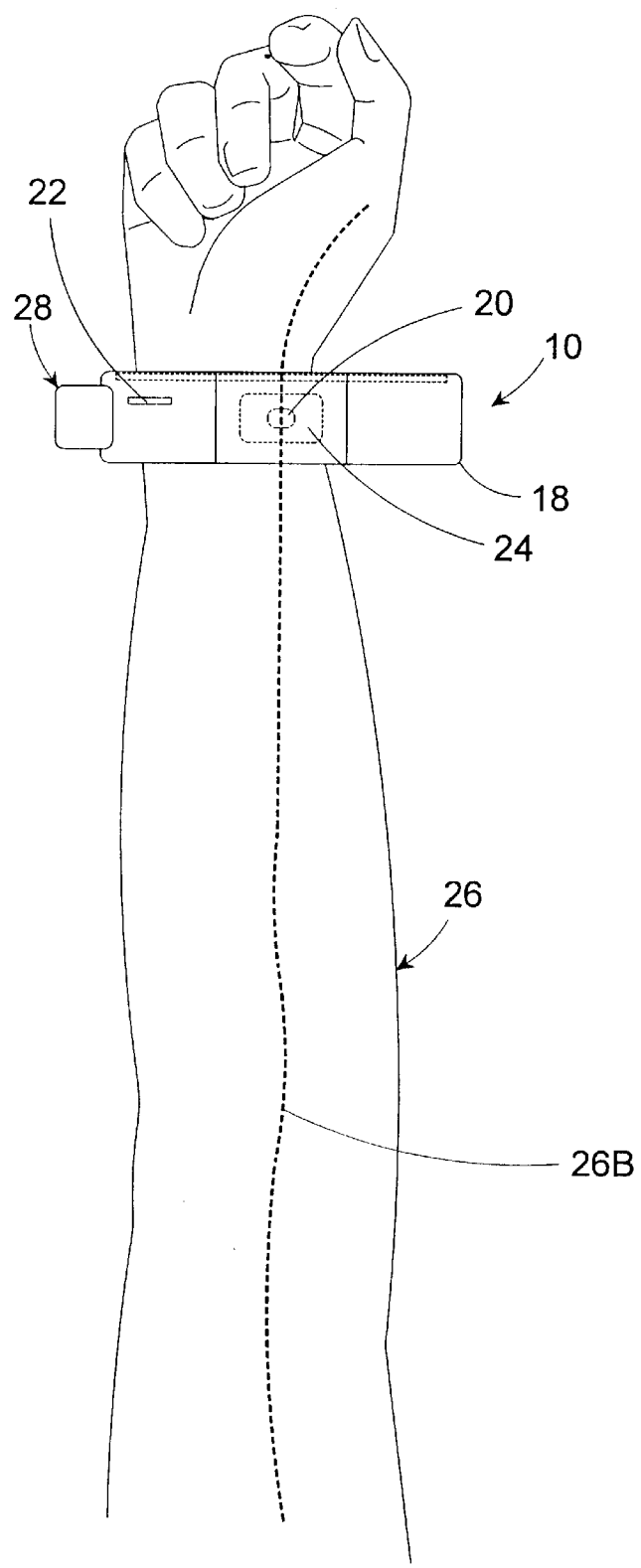
FIG. 2A is a top view of an artery locating device positioned on a patient's arm epidermis on top of a patient's arm radial artery.

Referring to FIG. 2 and FIG. 2A which are a side view and a top view of an artery locating device (10) positioned on a patient's arm epidermis (26A) on top of a patient's arm radial artery (26B). The cross sectional view of the patient's arm (26) exhibits a patient's arm bone (26D) having patient's arm muscles (26C) circumferentially positioned there around. The housing bottom (18B) has a concave curvature complimentary to a convex curvature of a patient's arm (26). When an user positions the artery locating device (10) on a patient's arm epidermis (26A) of a patient's arm (26) moving laterally until the artery sensor (20) is positioned directly over a patient's arm radial artery (26B) which sends an electronic signal to the microchip (22) which in turn sends an electronic signal to the artery monitor visual display indicator light (16AA) of the artery monitor visual display (16A) which functions to illuminate the artery monitor visual display indicator light (16AA). Simultaneously, the microchip (22) sends an electronic signal to heart rate monitor visual display indicator light (12CA) which functions to illuminate the heart rate monitor visual display indicator light (12CA). Simultaneously, the microchip (22) sends an electronic signal to the heart rate monitor LCD display (12B) which displays a patient's heart rate. Simultaneously, the microchip (22) sends an electronic signal to the pulse intensity monitor visual display indicator light (14CA) which functions to illuminate the pulse intensity monitor visual display indicator light (14CA). Simultaneously, the microchip (22) sends an electronic signal to the pulse intensity monitor LCD display (14B) which displays the patient's pulse intensity.

Lastly, referring to FIG. 3 which is a diagrammatic representation of a method (1 10) of utilizing an artery locating device (10) consisting of the following steps:

A) placing (112) a housing bottom (18B) of an artery locating device (10) on a patient's arm epidermis (26A);

B) first moving (114) the artery locating device (10) laterally until a patient's arm radial artery (26B) is detected by an artery sensor (20) activating an artery monitor (16); and C) second moving (116) the artery locating device (10) laterally until a patient's arm radial artery (26B) is centered by indication of an artery monitor visual display indicator light (16AA) of an artery monitor visual display (16A).

It will be understood that each of the elements described above, or two or more together, may also find a useful application in other types of constructions differing from the type described above.

While the invention has been illustrated and described as embodied in an artery locating device, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

1. An artery locating and monitoring device (10) comprising:
   A) a housing (18) which comprises a housing power means access (18A), a housing bottom (18B), a housing front (18F), and a housing rear (18R);
   B) a microchip (22) contained within the housing (18);
   C) a power means (24) electronically connected to the microchip (22), the power means (24) contained within the housing (18) having the housing power means access (18A) removably positioned there over for providing electrical power for said device;
   D) a heart rate monitor (12) contained within the housing (18), the heart rate monitor (12) comprises a heart rate monitor LCD display (12B) which is electronically connected to the microchip (22), the heart rate monitor (12) further comprises a heart rate monitor visual display (12C) having a heart rate monitor visual display indicator light (12CA) which is electronically connected to the microchip (22);
   E) a pulse intensity monitor (14) contained within the housing (18), the pulse intensity monitor (14) comprises a pulse intensity monitor LCD display (14B) which is electronically connected to the microchip (22), the pulse intensity monitor (14) further comprises a pulse intensity monitor visual display (14C) having a pulse intensity monitor visual display indicator light (14CA) which is electronically connected to the microchip (22);
   F) an artery monitor (16) contained with the housing (18), the artery monitor (16) comprises an artery monitor visual display (16A) which is electronically connected to the microchip (22), the artery monitor (16) further comprises an artery monitor visual display indicator light (16AA) which is electronically connected to the microchip (22);
   G) an artery sensor (20) contained within the housing (18) positioned at the housing bottom (18B), the artery sensor (20) electronically connected to the microchip (22) for sensing said arm radial artery (26B), a user positioning the artery locating device (10) on a patient's arm (26) moving laterally until the artery sensor (20) is positioned directly over said patient's arm radial artery (26B) said microchip (22) sending an electronic signal to the artery monitor visual display indicator light (16AA) of the artery monitor visual display (16A) which functions to illuminate the artery monitor visual display indicator light (16AA), simultaneously, the microchip (22) sending an electronic signal to heart rate monitor visual display indicator light (12CA) which functions to illuminate the heart rate monitor visual display indicator light (12CA), simultaneously, the microchip (22) sending an electronic signal to the heart rate monitor LCD display (12B) which displays a patient's heart rate, simultaneously, the microchip (22) sending an electronic signal to the pulse intensity monitor visual display indicator light (14CA) which functions to illuminate the pulse intensity monitor visual display indicator light (14CA), simultaneously, the microchip (22) sending an electronic signal to the pulse intensity monitor LCD display (14B) which displays the patient's pulse intensity; and
   H) a digital finger clip (28) attached to housing (18), the digital finger clip (28) being electrically connected to microchip (22), when the patient inserts a finger into digital finger clip (28) an electronic signal is sent to microchip (22) which in turn sends an electronic signal to the artery monitor visual display indicator light (16AA) of the artery monitor visual display (16A) which functions to illuminate the artery monitor visual display indicator light (16AA), simultaneously, the microchip (22) sending an electronic signal to heart rate monitor visual display indicator light (12CA) which functions to illuminate the heart rate monitor visual display indicator light (12CA), simultaneously, the microchip (22) sending an electronic signal to the heart rate monitor LCD display (12B) which displays a patient's heart rate, simultaneously, the microchip (22) sending an electronic signal to the pulse intensity monitor visual display indicator light (14CA) which functions to illuminate the pulse intensity monitor visual display indicator light (14CA), simultaneously, the microchip (22) sending an electronic signal to the pulse intensity monitor LCD display (14B) which displays the patient's pulse intensity.

2. The artery locating device (10) as described in claim 1, wherein the heart rate monitor (12) further comprises heart rate monitor indicia (12A) printed thereon.

3. The artery locating device (10) as described in claim 2, wherein the heart rate monitor (12) is positioned on the housing front (18F).

4. The artery locating device (10) as described in claim 1, wherein the pulse intensity monitor (14) further comprises pulse intensity monitor indicia (14A) printed thereon.

5. The artery locating device (10) as described in claim 4, wherein the pulse intensity monitor (14) is positioned on the housing front (18F).

6. The artery locating device (10) as described in claim 1, wherein the artery monitor (16) is positioned on the housing front (18F).

7. The artery locating device (10) as described in claim 1, wherein the power means (24) is positioned on within the housing rear (18R) having the housing power means access (18A) positioned there over.

8. The artery locating device (10) as described in claim 1, wherein the housing (18) is constructed from a material selected from a group consisting of metal, metal alloy, plastic, plastic composite, rubber, rubber composite, fiberglass, epoxy, and carbon-graphite.

9. The artery locating device (10) as described in claim 1, wherein the housing bottom (18B) is concave in configuration which is complementary to a convex configuration of the patient's arm (26).

10. An artery locating and monitoring device (10) comprising:
   A) a housing (18) which comprises a housing power means access (18A), a housing bottom (18B), a housing front (18F), and a housing rear (18R);
   B) a microchip (22) contained within the housing (18);
   C) a power means (24) electronically connected to the microchip (22), the power means (24) contained within the housing (18) having the housing power means access (18A) removably positioned there over for providing electrical power for said device;
   D) a heart rate monitor (12) contained within the housing (18), the heart rate monitor (12) comprising a heart rate monitor LCD display (12B) which is electronically connected to the microchip (22), the heart rate monitor (12) further comprises a heart rate monitor visual display (12C) having a heart rate monitor visual display indicator light (12CA) which is electronically connected to the microchip (22);

E) a pulse intensity monitor (14) contained within the housing (18), the pulse intensity monitor (14) comprises a pulse intensity monitor LCD display (14B) which is electronically connected to the microchip (22), the pulse intensity monitor (14) further comprises a pulse intensity monitor visual display (14C) having a pulse intensity monitor visual display indicator light (14CA) which is electronically connected to the microchip (22);

F) an artery monitor (16) contained within the housing (18), the artery monitor (16) comprises an artery monitor visual display (16A) which is electronically connected to the microchip (22), the artery monitor (16) further comprises an artery monitor visual display indicator light (16AA) which is electronically connected to the microchip (22);

G) an artery sensor (20) is contained within the housing (18) positioned at the housing bottom (18B), the artery sensor (20) electronically connected to the microchip (22) for sensing said arm radial artery (26B), a user positioning the artery locating device (10) on a patient's arm (26) moving laterally until the artery sensor (20) is positioned directly over said patient's arm radial artery (26B) said microchip (22) sending an electronic signal to the artery monitor visual display indicator light (16AA) of the artery monitor visual display (16A) which functions to illuminate the artery monitor visual display indicator light (16AA), simultaneously, the microchip (22) sending an electronic signal to heart rate monitor visual display indicator light (12CA) which functions to illuminate the heart rate monitor visual display indicator light (12CA), simultaneously, the microchip (22) sending an electronic signal to the heart rate monitor LCD display (12B) which displays a patient's heart rate, simultaneously, the microchip (22) sending an electronic signal to the pulse intensity monitor visual display indicator light (12CA) which functions to illuminate the pulse intensity monitor visual display indicator light (14CA), simultaneously, the microchip (22) sending an electronic signal to the pulse intensity monitor LCD display (14B) which displays the patient's pulse intensity; and H) a digital clip (28) comprising a digital finger clip cylinder (28A) securely connected to an upper distal end of a digital finger clip connector (28B), a lower distal end of the digital finger clip connector (28B) movably connected to the housing (18) by a digital finger clip pivot pin (28C).

* * * * *